United States Patent
Johnson et al.

(10) Patent No.: US 6,215,014 B1
(45) Date of Patent: Apr. 10, 2001

(54) CATALYST COMPOSITION AND METHOD FOR PRODUCING DIARYL CARBONATES

(75) Inventors: Bruce Fletcher Johnson, Scotia; Kirill Vladimirovich Shalyaev, Clifton Park; Grigorii Lev Soloveichik, Latham; Eric James Pressman, East Greenbush, all of NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/383,424

(22) Filed: Aug. 27, 1999

(51) Int. Cl.⁷ .................................... C07C 68/00
(52) U.S. Cl. .................. 558/274; 558/271; 558/272; 558/273; 502/325; 502/339
(58) Field of Search .................... 558/271, 272, 558/273, 274

(56) References Cited

U.S. PATENT DOCUMENTS

| | | |
|---|---|---|
| 4,187,242 | 2/1980 | Chalk . |
| 5,231,210 | 7/1993 | Joyce et al. . |
| 5,239,106 | 8/1993 | Shafer . |
| 5,284,964 | 2/1994 | Pressman et al. . |
| 5,373,083 | 12/1994 | King et al. . |
| 5,380,907 | 1/1995 | Mizukami et al. . |
| 5,399,734 | 3/1995 | King et al. . |
| 5,498,789 | 3/1996 | Takagi et al. . |
| 5,502,232 | 3/1996 | Buysch et al. . |
| 5,543,547 | 8/1996 | Iwane et al. . |
| 5,726,340 | 3/1998 | Takagi et al. . |
| 5,760,272 | 6/1998 | Pressman et al. . |
| 5,821,377 | 10/1998 | Buysch et al. . |
| 5,856,554 | 1/1999 | Buysch et al. . |

FOREIGN PATENT DOCUMENTS

| | | |
|---|---|---|
| 736325 | 3/1996 | (DE) . |
| 071286 A1 | 2/1983 | (EP) . |
| 10158221 | 6/1980 | (JP) . |
| 94-271506 | 9/1994 | (JP) . |
| 94-271509 | 9/1994 | (JP) . |
| 95-145107 | 6/1995 | (JP) . |
| 96-89810 | 4/1996 | (JP) . |
| 96-92168 | 4/1996 | (JP) . |
| 96-193056 | 7/1996 | (JP) . |
| 97-110804 | 4/1997 | (JP) . |
| 97-255629 | 9/1997 | (JP) . |
| 97-278715 | 10/1997 | (JP) . |
| 97-278716 | 10/1997 | (JP) . |

OTHER PUBLICATIONS

Abstract of Japanese Patent 10316627 –Derwent Publications Ltd., London, GB., No. 1999–076424.

*Primary Examiner*—Michael G. Ambrose
(74) *Attorney, Agent, or Firm*—Noreen C. Johnson; Douglas E. Stoner

(57) ABSTRACT

Hydroxyaromatic compounds such as phenol are carbonylated with oxygen and carbon monoxide in the presence of a catalyst system comprising a Group VIIIB metal, preferably palladium; an alkali metal or alkaline earth metal halide, preferably sodium bromide; and at least one sulfone such as sulfolane. The catalyst system also preferably contains a compound of another metal, preferably lead.

18 Claims, No Drawings

CATALYST COMPOSITION AND METHOD FOR PRODUCING DIARYL CARBONATES

BACKGROUND OF THE INVENTION

This invention relates to the preparation of diaryl carbonates by carbonylation. More particularly, it relates to the improvement of diaryl carbonate yield in the carbonylation reaction.

Diaryl carbonates are valuable intermediates for the preparation of polycarbonates by transesterification with bisphenols in the melt. This method of polycarbonate preparation has environmental advantages over methods which employ phosgene, a toxic gas, as a reagent and environmentally detrimental chlorinated aliphatic hydrocarbons such as methylene chloride as solvents.

Various methods for the preparation of diaryl carbonates by an oxidative carbonylation (hereinafter sometimes simply "carbonylation" for brevity) reaction of hydroxyaromatic compounds with carbon monoxide and oxygen have been disclosed. In general, the carbonylation reaction requires a rather complex catalyst. Reference is made, for example, to U.S. Pat. No. 4,187,242, in which the catalyst is a heavy Group VIII metal; i.e., a Group VIII metal having an atomic number of at least 44, said metals consisting of ruthenium, rhodium, palladium, osmium, iridium and platinum, or a complex thereof.

The production of carbonates may be improved by including a metal-based cocatalyst along with the heavy Group VIII metal catalyst. Although the identity of suitable metal-based cocatalysts will depend on specific reaction conditions including the identity of reactants and other members of the catalyst package, some general guidance can be found in U.S. Pat. Nos. 4,187,242 and 4,201,721.

A further development in the carbonylation reaction, including the use of specific lead compounds as cocatalysts, is disclosed in U.S. Pat. No. 5,498,789. Also required according to that patent is the use of quaternary ammonium or phosphonium halides, as illustrated by tetra-n-butylammonium bromide, as part of the catalyst package. Compounds characterized as inert solvents, such as toluene, diethyl ether, diphenyl ether and acetonitrile, can also be present.

The commercial viability of the carbonylation reaction would be greatly increased if a less expensive compound could be substituted for the quaternary ammonium or phosphonium halide. Substitution of such compounds as sodium bromide, however, result in the isolation of the desired diaryl carbonate in low or insignificant yield.

It is of interest, therefore, to develop catalyst systems which include an inexpensive halide compound and which can efficiently produce diaryl carbonates. Some such systems are known. Reference is made, for example, to Japanese Kokai 10/316,627, which discloses the use of palladium and a lead or manganese compound in combination with a halide such as sodium bromide and with an amide or alkylurea. U.S. Pat. No. 5,726,340 and Japanese Kokai 9/278,716 disclose similar systems in which the lead is combined with another metal and in which inert solvents such as those mentioned hereinabove may be present. The development of other systems employing relatively inexpensive halides, however, remains desirable.

SUMMARY OF THE INVENTION

The present invention provides a method for preparing diaryl carbonates which includes a relatively inexpensive halide and a compound which maximizes the effectiveness of said halide. Also provided is a catalyst composition useful in such a method.

In one of its aspects, the invention provides a method for preparing a diaryl carbonate which comprises contacting at least one hydroxyaromatic compound with oxygen and carbon monoxide in the presence of an amount effective for carbonylation of at least one catalytic material comprising:

(A) a Group VIII metal having an atomic number of at least 44 or a compound thereof, (B) at least one alkali metal halide or alkaline earth metal halide, and (C) at least one sulfone.

Another aspect of the invention is catalyst compositions comprising components A, B and C as described above, and any reaction products thereof.

DETAILED DESCRIPTION; PREFERRED EMBODIMENTS

Any hydroxyaromatic compound may be employed in the present invention. Monohydroxyaromatic compounds, such as phenol, the cresols, the xylenols and p-cumylphenol, are generally preferred with phenol being most preferred. The invention may, however, also be employed with dihydroxyaromatic compounds such as resorcinol, hydroquinone and 2,2-bis(4-hydroxyphenyl)propane or "bisphenol A", whereupon the products are polycarbonate oligomers.

Other reagents in the method of this invention are oxygen and carbon monoxide, which react with the phenol to form the desired diaryl carbonate. They may be employed in high purity form or diluted with another gas such as nitrogen, argon, carbon dioxide or hydrogen which has no negative effect on the reaction.

For the sake of brevity, the constituents of the catalyst system are defined as "components" irrespective of whether a reaction between said constituents occurs before or during the carbonylation reaction. Thus, the catalyst system may include said components and any reaction products thereof.

Component A of the catalyst system is one of the heavy Group VIII metals, preferably palladium, or a compound thereof. Thus, useful palladium materials include elemental palladium-containing entities such as palladium black, palladium/carbon, palladium/alumina and palladium/silica; palladium compounds such as palladium chloride, palladium bromide, palladium iodide, palladium sulfate, palladium nitrate, palladium acetate and palladium 2,4-pentanedionate; and palladium-containing complexes involving such compounds as carbon monoxide, amines, nitrites, phosphines and olefins. Preferred in many instances are palladium(II) salts of organic acids, most often $C_{2-6}$ aliphatic carboxylic acids, and palladium(II) salts of β-diketones. Palladium(II) acetate and palladium(II) 2,4-pentanedionate are generally most preferred. Mixtures of the aforementioned palladium materials are also contemplated.

Component B is at least one alkali metal or alkaline earth metal halide, preferably a bromide such as lithium bromide, sodium bromide, potassium bromide, calcium bromide or magnesium bromide. Alkali metal bromides are especially preferred, with sodium bromide often being most preferred by reason of its particular suitability and relatively low cost.

Component C is at least one sulfone, which may be aliphatic, aromatic or heterocyclic. Illustrative sulfones are dimethyl sulfone, diethyl sulfone, diphenyl sulfone and sulfolane (tetrahydrothiophene-1,1-dioxide). Sulfolane is often preferred.

In a highly preferred embodiment of the invention, there is also present in the catalyst system (D) at least one cocatalyst which is a compound of a metal other than a heavy Group VIII metal. This metal is preferably one which is soluble in the liquid phase under the reaction conditions. Numerous other metal compounds are known in the art to be active as carbonylation cocatalysts, and any compound having such activity may be used according to the present invention provided an improvement in diphenyl carbonate production, usually yield, is achieved thereby.

Illustrative cocatalytic metals include titanium, copper, zinc and lead, which may be used singly or in combination. For the purposes of this invention the preferred cocatalysts are those containing metals other than Group VIII metals; that is other than iron, cobalt and nickel. More preferred are compounds of lead, particularly when used alone or in combination with titanium. It should be noted, however, that component C is not effective to optimize diaryl carbonate formation for all possible permutations of component D; the combined effectiveness of the two for this purpose may be determined by simple experimentation.

Examples of lead compounds which may be employed are lead oxides such as PbO and $Pb_3O_4$; inorganic lead salts such as lead(II) nitrate; lead carboxylates such as lead(II) acetate and lead(II)propionate; lead alkoxides and aryloxides such as lead(II) methoxide and lead(II) phenoxide; and lead salts of β-diketones such as lead(II) 2,4-pentanedionate. Mixtures of the aforementioned lead compounds may also be employed. The preferred lead compounds are lead(II) oxide, lead(II) aryloxides and lead(II) 2,4-pentanedionate.

Examples of titanium compounds are inorganic titanium salts such as titanium(IV) bromide; titanium alkoxides and aryloxides such as titanium(IV) butoxide and titanium(IV) phenoxide; and titanium salts of β-diketones such as titanium(IV) oxide bis(2,4-pentanedionate). Mixtures of the aforementioned titanium compounds may also be employed. The preferred titanium compounds are titanium(IV) alkoxides, aryloxides and 2,4-pentanedionates.

The preferred compounds of other metals are, for the most part, salts of β-diketones and especially 2,4-pentanedionates. In addition to the aforementioned reactants and catalyst system, it is strongly preferred for a desiccant to be present in the reaction system. The preferred desiccants are non-reactive materials such as molecular sieves, as illustrated by 3-★ngstrom (hereinafter "3 A") molecular sieves. They are usually isolated from the other reactants, as by presence in a basket mounted to a stirrer shaft or the like.

Component A is most often present in the amount of about 0.1–10,000 ppm by weight of the appropriate Group VIII metal (usually palladium), based on the total of hydroxyaromatic compound and component C, and component B in the amount of about 1–2,000 mmol per equivalent of the Group VIII metal of component A. Component D, when employed, is generally present in the amount of about 1–200 gram-atoms of total metal per equivalent of the Group VIII metal of component A.

The role of component C in the composition and method of the invention is believed to be to increase the degree of dissociation and ionization of the halide anion of component B, perhaps by forming a complex with the cationic portion of said component, although the invention is in no way dependent on this or any other theory of operation. The amount of component C employed will be an amount effective to increase the yield of the desired diary carbonate as evidenced, for example, by an increase in "turnover number"; i.e., the number of moles of diaryl carbonate formed per gram-atom of palladium present. This amount is most often about 1–60% by volume based on the total of hydroxyaromatic compound and component C.

The method of the invention is preferably conducted in a reactor in which the hydroxyaromatic compound and catalyst system are charged under pressure of carbon monoxide and oxygen and heated. The reaction pressure is most often within the range of about 1–500 and preferably about 1–150 atm. Gas is usually supplied in proportions of about 1–50 mole percent oxygen with the balance being carbon monoxide, and in any event outside the explosion range for safety reasons. The gases may be introduced separately or as a mixture. Reaction temperatures in the range of about 60–150° C. are typical. In order for the reaction to be as rapid as possible, it is preferred to substantially maintain the total gas pressure and partial pressure of carbon monoxide and oxygen, as described, for example, in U.S. Pat. No. 5,399,734, until conversion of the hydroxyaromatic compound is complete.

The diaryl carbonates produced by the method of the invention may be isolated by conventional techniques. It is often preferred to form and thermally crack an adduct of the diaryl carbonate with the hydroxyaromatic compound, as described in U.S. Pat. Nos. 5,239,106 and 5,312,955.

The method of the invention is illustrated by the following examples. Minor variations in reagent amounts from one example to another are not believed significant from the standpoint of yield.

EXAMPLES 1–4

Carbonylation experiments were conducted in small vials, employing palladium(II) 2,4-pentanedionate, sodium bromide and sulfolane at levels of 24 ppm of palladium based on phenol, 270 equivalents of sodium bromide per equivalent of palladium and 1 part sulfolane by volume per 1.86 parts of phenol. Various cocatalyst compounds which included lead(II) oxide, titanium(IV) oxide bis(2,4-pentanedionate), zinc 2,4-pentanedionate and copper(II) 2,4-pentanedionate, employed alone or in combination, were employed as component D. Each vial was capped with snap caps having a slit with a polytetrafluoroethylene septum and the vials were placed in an autoclave which was pressurized to 81.6 atm with a mixture of 91.7 mole percent carbon monoxide and 8.3 mole percent oxygen and heated at 100° C. for 3 hours. The contents of the vials were analyzed for diphenyl carbonate by vapor phase chromatography.

The results are given in the following table, as averages for duplicate runs. Cocatalyst proportions are in equivalents per equivalent of palladium, and sulfolane proportions are in percent by volume based on phenol. Comparison is made to two controls per example: Control 1 in which no sulfolane was used and the proportion of phenol was increased correspondingly, and Control 2 in which the same was true and the sodium bromide was replaced by an equivalent amount of tetraethylammonium bromide.

| Example | 1 | 2 | 3 | 4 |
| --- | --- | --- | --- | --- |
| Cocatalyst metal (gram-atoms) | Pb (48) | Pb (48), Ti (11) | Ti (11), Zn (12) | Cu (11) |
| Turnover number: | | | | |
| Example | 1530 | 1797 | 727 | 279 |
| Control 1 | 152 | 472 | 305 | 227 |
| Control 2 | 716 | 2625 | 717 | 1074 |

It is apparent that the use of sulfolane affords in each example an improvement over the control which did not employ sulfolane, with the improvement ranging from modest in Example 4 to very significant in Examples 1 and 2. In Examples 2 and 3, turnover numbers were close enough to those of Control 2, employing the more expensive quaternary ammonium bromide, to invite comparison.

What is claimed is:

1. A method for preparing a diaryl carbonate which comprises contacting at least one hydroxyaromatic compound with oxygen and carbon monoxide in the presence of an amount effective for carbonylation of at least one catalytic material comprising:

(A) a Group VIII metal having an atomic number of at least 44 or a compound thereof, (B) at least one alkali metal halide or alkaline earth metal halide, and (C) at least one sulfone.

2. A method according to claim 1 wherein there is also present (D) at least one cocatalyst which is a compound of a non-Group VIIIB metal.

3. A method according to claim 2 wherein the hydroxyaromatic compound is phenol.

4. A method according to claim 2 wherein the Group VIIIB metal in component A is palladium.

5. A method according to claim 4 wherein component A is palladium(II) acetate or palladium(II) 2,4-pentanedionate.

6. A method according to claim 2 wherein component D is lead(II) oxide, a lead(II) aryloxide or lead(II) 2,4-pentanedionate.

7. A method according to claim 2 wherein component D is lead(II) oxide, a lead(II) aryloxide or lead(II) 2,4-pentanedionate combined with a titanium(IV) alkoxide, aryloxide or 2,4-pentanedionate.

8. A method according to claim 2 wherein component D is zinc oxide combined with a titanium(IV) alkoxide, aryloxide or 2,4-pentanedionate.

9. A method according to claim 2 wherein component D is copper(II) 2,4-pentanedionate.

10. A method according to claim 2 wherein component B is an alkali metal bromide.

11. A method according to claim 10 wherein component B is sodium bromide.

12. A method according to claim 1, wherein component C is a heterocyclic sulfone.

13. A method according to claim 12, wherein component C is sulfolane.

14. A method according to claim 1 wherein a desiccant is also present.

15. A method according to claim 2 wherein component A is present in the amount of about 0.1–10,000 ppm by weight of said Group VIII metal based on the total of hydroxyaromatic compound and component C, component B in the amount of about 1–2,000 mmol per equivalent of the Group VIII metal of component A, component C in the amount of 1–60% by volume based on the total of hydroxyaromatic compound and component C, and component D in the amount of about 1–200 gram-atoms of total metal per equivalent of the Group VIII metal of component A.

16. A method according to claim 2 wherein the proportion of oxygen is about 1–50 mole percent based on total oxygen and carbon monoxide.

17. A method according to claim 2 wherein a pressure in the range of about 1–500 atm and a temperature in the range of about 60–150° C. are maintained.

18. A method for preparing diphenyl carbonate which comprises contacting phenol with oxygen and carbon monoxide in the presence of an amount effective for carbonylation of at least one catalytic material comprising:

(A) palladium or a compound thereof, (B), sodium bromide, (C) sulfolane, and (D) at least one lead compound.

* * * * *